United States Patent [19]

Schnell

[11] 4,005,062
[45] Jan. 25, 1977

[54] PROCESS OF PREPARING WATER-SOLUBLE WHIPPABLE EXTRACT FROM MICROORGANISM PROTEIN MATERIAL

[75] Inventor: Philip G. Schnell, Wheaton, Ill.

[73] Assignee: Standard Oil Company (Indiana), Chicago, Ill.

[22] Filed: Aug. 16, 1974

[21] Appl. No.: 497,844

[52] U.S. Cl. .................. 260/112 R; 426/564; 426/568; 426/570; 426/572
[51] Int. Cl.$^2$ ................ A23J 1/18; A23J 3/02
[58] Field of Search .................. 260/112 R

[56] References Cited
UNITED STATES PATENTS

| | | | |
|---|---|---|---|
| 3,585,179 | 6/1971 | Samejima et al. | 260/112 R |
| 3,615,654 | 10/1971 | Ayukawa | 426/230 |
| 3,725,075 | 4/1973 | Muroi et al. | 260/112 R X |
| 3,833,552 | 9/1974 | Akin | 260/112 R |
| 3,862,109 | 1/1975 | Mitsuda et al. | 260/112 R |
| 3,862,112 | 1/1975 | Ishida et al. | 260/112 R |

OTHER PUBLICATIONS

Chem. Abstracts, vol. 80, 1974, 25939c, Ishida et al. 25939c–effective date 9/73.

*Primary Examiner*—Howard E. Schain
*Attorney, Agent, or Firm*—Werten F. W. Bellamy; Arthur G. Gilkes; William T. McClain

[57] ABSTRACT

The extraction and production of whippable product from microbial cells is obtained by a process involving temperature, slurrying, and separation treatments.

13 Claims, No Drawings

PROCESS OF PREPARING WATER-SOLUBLE WHIPPABLE EXTRACT FROM MICROORGANISM PROTEIN MATERIAL

BACKGROUND OF THE INVENTION

Recent concern for the welfare of the world population has included consideration of additional means for feeding the rapidly increasing number of people involved. The problem embraces providing both adequate per capita caloric intake and a balanced diet, with particular reference to the acknowledged lack of sufficient protein-affording foods in many parts of the world. One means for providing necessary protein supplies is through the growth of single-cell protein-affording microorgansims, such as yeasts, bacteria and algae, for use as either foods or food supplements.

Production of single-cell protein (SCP) materials in large quantity may be accomplished by fermentation processes employing, for example, carbohydrate, hydrocarbon or oxygenated hydrocarbon materials as substrate. Principal requirements are that the substrate material be inexpensive and readily consumed by the selected microorganism so that process costs are not excessive. Equally important is the acceptability and utility of the SCP material as a food or food component. These latter considerations include taste and odor factors relating to public acceptance as well as metabolic and toxicity factors relating to suitability of SCP material for inclusion in the human diet.

Both the technical and the patent literature describe fermentation processes for production of microorganisms which readily afford useful SCP materials. For example, yeasts have been grown on the carbohydrates contained in waste sulfite liquor, the normal alkane components of a gas oil hydrocarbon fuel, and on a mixture of oxygenated hydrocarbons. Production of bacteria has been similarly described. Fermentation to produce yeasts or bacteria comprises an oxidation process, evolving much heat and requiring both substantial oxygen transfer and good control of fermentation temperature. Preferred substrate materials will already contain as much combined oxygen as possible in order to minimize the heat release and the oxygen requirement. Production of foodgrade SCP material may also require an extraction step to limit the presence of undersirable, residual substrate material such as high-molecular-weight hydrocarbons or slowly fermented oxygenated hydrocarbon species.

A number of the fermentation processes planned or in use currently for production of SCP material are intended to provide primarily an animal feed supplement and hence to supply protein for human consumption only indirectly. However, some microorganisms, notably certain yeasts within the *Saccharomycetoideae* and *Cryptococcoideae* sub-families, have been approved by the Food and Drug Administration for direct use in foods intended for human consumption.

SCP materials may be utilized as whole cells or may be processed to recover protein or protein hydrolyzates for inclusion in various food products. The whole-cell material typically is deficient in desirable functional properties, being powdery small cells (1–10 micron dimensions) which do not form a cohesive structured mass. The protein content of cells may largely be recovered by rupture or destruction of the cell wall, as by application of shearing forces or autolytic treatment with enzymes. Such proteins are usually concentrated by adjusting the pH to the isoelectric point and separating as by filtration or centrifugation. The hydrolyzates comprise chemically degraded protein material rich in the amino acid moieties which normally combine together to form the protein macromolecules.

Desirable functional properties in SCP materials include lowdispersibility in water, good water retention, oil absorption and retention, heat coagulation and emulsion stabilization. Water-soluble protein materials, intended for replacement or supplementation of egg albumin, should exhibit good whippability providing a large and stable foamed mass.

SUMMARY OF THE INVENTION

It is the object of this invention to provide a water-soluble protein material, derived from single-cell protein, suitable for use in whipped food products.

I have found that treatment of unicellular microorganisms, particularly bacteria, fungi and yeasts, with water at controlled elevated temperatures for limited time provides a highly whippable protein material.

More specifically, I prefer to prepare on aqueous slurry of microbial cells, heat the slurry to about 30° to about 35° C, separate the heated slurry into a solid and liquid phase, reslurry the solid phase in water, heat the reslurried solid phase to about 80° to about 100° C for about 45 to 75 minutes, separate the heated slurry into solid phase and aqueous supernatant phase comprising a water-soluble protein fraction, recover the water-soluble protein fraction and freeze dry the water-soluble protein fraction. The dried water-soluble protein fraction exhibits a higher foam expansion and foam stability then egg white, non-fat dry milk, and pregelatinized starch or flour. Additionally, the water-soluble protein fraction may be combined with egg white or non-fat dry milk to increase their foam expansion and stability properties.

DESCRIPTION OF THE INVENTION

This invention discloses a novel method for providing an improved water-soluble protein fraction exhibiting excellent whippability properties in preparing food products for human consumption.

It has been found that suitable protein material can be obtained from single-cell protein sources by subjecting aqueous microbial cells to aqueous slurrying, solid-liquid phase separation, and controlled elevated temperatures for limited periods of time. Although the cell wall remains intact most of the protein content of the cell is extracted into the aqeous supernatant phase. The aqeous slurry contains from 1 to 20 wt. % (dry basis) of microbial cells. The slurry is initially heated to about 30° to about 35° C. and then separated into a solid phase comprising residual cell material and a liquid supernatant phase comprising pigment and color ingredients; reslurrying the residual cell material by adding water; heating the reslurried residual cell material at temperatures of about 80° to 100° C. for a time period of about 45 to 75 minutes; separating the heated slurry into a solid phase comprising residual cell material and an aqueous supernatant phase comprising a water-soluble protein fraction; recovering the water-soluble protein fraction; and drying the water-soluble protein fraction to produce a product having light color, high foam expansion and stability, bland taste and heat stability.

The practice of this invention is broadly applicable to microorganisms and particularly those organisms classified as those listed in Table I, yeasts such as those listed in Table II and fungi suc as those listed in Table III are suitable microorganisms.

TABLE I — Suitable Bacteria

*Acetobacter sp.*
*Arthrobacter sp.*
*Bacillus subtilus*
*Corynebacteria sp.*
*Micrococcus sp.*
*Pseudomonas sp.*

TABLE II — Suitable Yeasts

*Candida curvata*
*Candida lipolytica*
*Candida pulcherima*
*Candida utilis*
*Hansenula anomala*
*Hansenula miso*
*Oidium lactis*
*Saccharomyces carlsbergensis*
*Saccharomyces fragilis*
*Trichosporon cutaneum*
*Saccharomyces cerevisiae*
*Candida parapsilosis*
*Hansenula wickerhamii*
*Pichia pastoris*
*Pichia haplophyla*

TABLE III

| Suitable Fungi | |
|---|---|
| *Aspergillus niger* | *Penicillium notatum* |
| *Aspergillus glaucus* | *Penicillium chrysogenum* |
| *Aspergillus oryzae* | *Penicillium glaucum* |
| *Aspergillus terreus* | *Penicillium griseofulvum* |
| *Aspergillus itaconicus* | |

*Candida utilis, Saccharomyces cerevisiae, Saccharomyces, fragilis,* and *Saccharomyces carlsbergensis* are preferred starting materials for the process of this invention, however, because each has been generally regarded as safe by the F.D.A. for use in food products.

This invention may be applied to either isolated cellular material or to cells newly grown in a fermentation process. Where the cellular material has been previously isolated it should be slurried with water to provide the desired cell concentration. Where fresh cells are employed the fermentor effluent may be concentrated, as by centrifugation, to provide a suitable slurry.

The concentration of cellular SCP material suspended in the aqueous acid solution may vary within the range from 1 to 20 wt. % (dry basis) and is preferably held within the range from 3 to 10 wt. % (dry basis) cells.

The process for the isolation of a whippable protein fraction from microbial cells requires the following treatment.

Initially, an aqueous slurry containing from 1 to 20 wt. % (dry basis) microbial cells is prepared. Preferably, the amount of microbial cells is in the range of 5 to 15 wt. % (dry basis).

Next, the aqueous slurry of microbial cells is heated to temperatures ranging from 30° to 35° C. However, the temperature of 32° C. has been found highly suitable.

The heated slurry of cells is then separated into solid and liquid phases. This separation can be effected by centrifugation or other solidliquid phase separation methods. The solid phase is comprised of residual cell material and the liquid supernatant phase is comprised of pigment and color ingredients.

The solid phase comprising the residual cell material is reslurried by adding water.

Now, the reslurried residual cell material is heated at temperatures of about 80° to 100° C. for a time period of about 45 to 75 minutes. Heating the slurry at a temperature of 90° C. for 60 minutes is preferred.

The heated slurry of residual cell material is separated into a solid phase comprising the residual cell material and an aqueous supernatant phase, comprising the water-soluble protein fraction.

The solid phase comprising the residual cell material is separated and is available for use in other products prepared from yeast, bacteria or fungus cell material.

On the other hand, the aqeuous supernatant phase comprising the water-soluble protein fraction is recovered and then freeze-dried to produce a product having light color, high foam expansion and stability, bland taste and heat stability.

The protein concentrate provided by this invention is surprisingly effective in preparing whipped food products. The product of this invention has many beneficial advantages over other sources of whippable protein. The highly whippable product prepared in accordance with this invention does not require chemical or biological modification and is heat stable. The product can be used as an extension of a commodity, such as egg albumen, which is in short supply. Additionally, the product can be used in many food or other products such as meringues, divinity-type candy and souffles.

The process of this invention has the advantage of being able to extract color and flavor products from the 32° C. extract.

The following schematic diagram serves to illustrate the steps involved in the practice of this invention.

PROCESS FOR EXTRACTION AND PRODUCTION OF
WHIPPABLE PRODUCT FROM YEAST CREAM OR SLURRIED YEAST

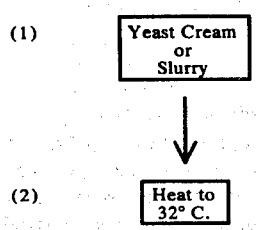

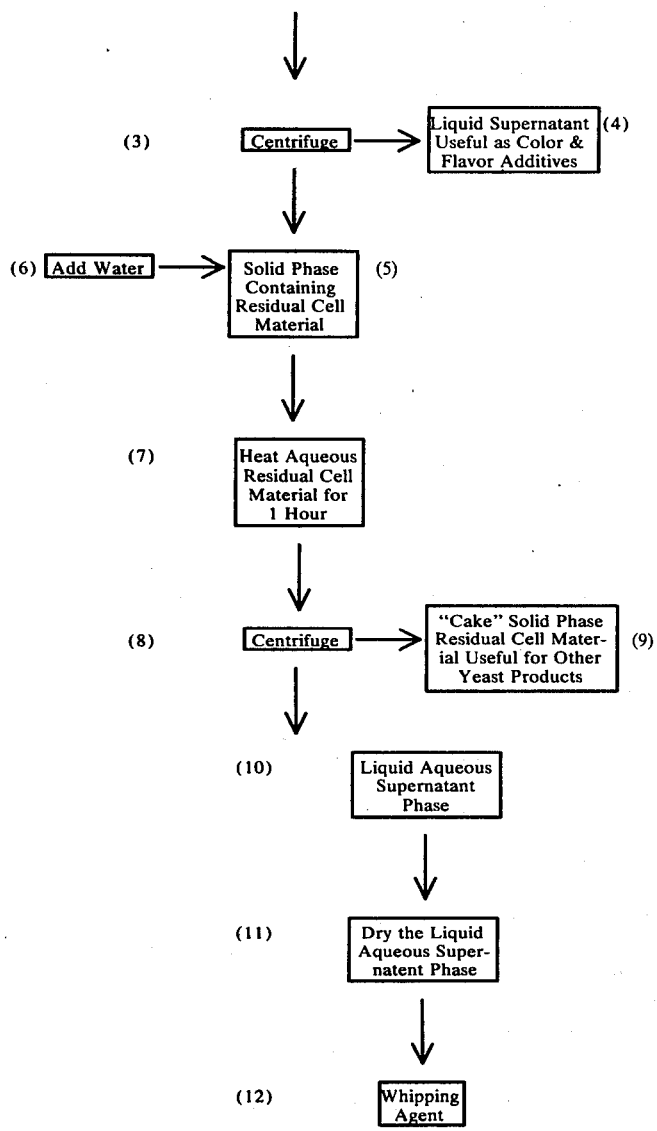

SPECIFIC EMBODIMENTS OF THE INVENTION

The following example is illustrative, without implied limitation, of my invention.

EXAMPLE

A 10 liter aqueous solution of yeast *Candida utilis* containing 10 wt. % cells on a dry basis was prepared. The aqueous solution was heated, using an immersion heater, to 32° C. The solution was then subjected to centrifugation using a Type AP 14 VH Sharples centrifuge, operating at 15,000 r.p.m. The recovered residual cell material was diluted with water to a volume of 10 liters. The aqueous solution of residual cell material was heated, using an immersion heater, to 90° C. and maintained for 1 hour. The heated solution was then subjected to centrifugation again using a Type AP 14 VH Sharples centrifuge operating at 15,000 r.p.m. The recovered water-soluble protein fraction was dried by freeze-drying. The resulting product had a light color, high foam expansion and stability, bland taste and heat stability.

The product prepared in accordance with this invention can be used to replace egg albumen in products foam expansion and as an extender to egg albumen in products requiring foam expansion and heat coagulability as shown in Table I.

TABLE I

| | WHIPPING PROPERTIES OF VARIOUS YEAST EXTRACTS AND OTHER FOOD PRODUCTS | | |
|---|---|---|---|
| | Sample | Foam Expansion (ml) | Foam Stability (ml)* |
| (1) | Egg Albumen (1%) | 50 | 40 |

TABLE I-continued
WHIPPING PROPERTIES OF VARIOUS YEAST EXTRACTS AND OTHER FOOD PRODUCTS

| | Sample | Foam Expansion (ml) | Foam Stability (ml)* |
|---|---|---|---|
| (2) | Non-fat Dried Milk (1%) | 52 | 0 |
| (3) | All-purpose Flour (1%) | 2 | 2 |
| (4) | 32° C Extract from Cream (1%) | 110 | 5 |
| (5) | 32° C Extract from Spray Dried Cells (1%) | 20 | 6 |
| (6) | 90° C Extract from Cream (1%) | 184 | 60 |
| (7) | 90° C Extract from Spray Dried Cells (1%) | 82 | 20 |
| (8) | 0.5% Egg Albumen 0.5% 90° C Extract (cream) | 190 | 129 |
| (9) | 0.5% Non-fat Dried Milk 0.5% 90° C Extract (cream) | 176 | 84 |
| (10) | 0.5% All-purpose Flour 0.5% 90° C Extract (cream) | 28 | 2 |

*Foam stability = volume after 30 minutes.

The properties for each of 10 yeast extracts and other food products given in Table I were determined by the following series of steps:

1. 100 ml. of a 1% aqueous solution of the sample material was prepared;
2. the solution was whipped at 0° C for 1 minute, using a Virtis 45 mixer, at the rate of 20,000 r.p.m.;
3. the contents from step (2) were added to a 300 ml. graduated cylinder and the amount of foam produced was measured (foam expansion) in the cylinder; and
4. the whipped sample was allowed to sit at 0° C. for 30 minutes and the foam volume was remeasured to determine the foam stability.

I claim:

1. A process for the isolation of a whippable protein fraction from microbial cells, consisting of the steps of:
   a. providing an aqueous slurry containing from 1 to 20 wt. % (dry basis) microbial cells;
   b. heating the slurry to a temperature within the range from about 30° to about 35° C.;
   c. separating the heated slurry into a solid phase comprising residual cell material and a liquid supernatant phase comprising pigment and color ingredients;
   d. reslurrying the residual cell material by adding water;
   e. heating the reslurried residual cell material at temperatures of about 80° to 100° C. for a time period of about 45 to 75 minutes.
   f. separating the heated slurry into a solid phase comprising residual cell material and an aqueous supernatant phase comprising a water-soluble protein fraction;
   g. recovering the water-soluble protein fraction; and
   h. drying the water-soluble protein fraction to produce a product having light color, high foam expansion and stability, bland taste and heat stability.

2. The process of claim 1 wherein the slurry is heated to a temperature of 32° C. in step (b).
3. The process of claim 1 wherein the reslurried cell material is heated to a temperature of 90° C. in step (e).
4. The process of claim 1 wherein the time period in step (e) is 60 minutes.
5. The process of claim 1 wherein the temperature in step (b) is 32° C. and the temperature in step (e) is 90° C.
6. The process of claim 3 wherein the time period in step (e) is 60 minutes.
7. The process of claim 6 wherein the temperature in step (b) is 32° C.
8. The process of claim 7 wherein the aqueous slurry in step (a) contains from 5 to 15 wt. % (dry basis) cells.
9. Thr process of claim 1 wherein the aqueous slurry in step (a) contains from 5 to 15 wt. % (dry basis) cells.
10. The process of claim 1 wherein the microbial cells are grown in an aerobic fermentor in a fermentation broth mineral nutrient medium and the fermentor effluent is centrifuged to separate excess fermentation broth and provide a slurry comprising from 1 to 20 wt. % (dry basis) cells.
11. The process of claim 1 wherein the micorbial cells are selected from the class consisting of bacteria, fungi and yeasts.
12. The process of claim 7 wherein the yeast is *Saccharomyces carlsbergensis*, *Saccharomyces cerevisiae*, *Saccharomyces fragilis* or *Candida utilis*.
13. The process of claim 8 wherein the yeast is *Candida utilis*.

* * * * *